US 6,808,931 B1

United States Patent
Wang et al.

(10) Patent No.: US 6,808,931 B1
(45) Date of Patent: Oct. 26, 2004

(54) METHOD FOR THE DETERMINATION OF HEXAVALENT CHROMIUM USING ULTRASONICATION AND STRONG ANION EXCHANGE SOLID PHASE EXTRACTION

(75) Inventors: Jin Wang, Cincinnati, OH (US); Kevin Ashley, Cincinnati, OH (US)

(73) Assignee: The United States of America as represented by the Secretary of Health and Human Services, Washington, DC (US)

( * ) Notice: Subject to any disclaimer, the term of this patent is extended or adjusted under 35 U.S.C. 154(b) by 0 days.

(21) Appl. No.: 09/622,547

(22) PCT Filed: Feb. 25, 1999

(86) PCT No.: PCT/US99/04200

§ 371 (c)(1),
(2), (4) Date: Oct. 10, 2000

(87) PCT Pub. No.: WO99/44056

PCT Pub. Date: Sep. 2, 1999

Related U.S. Application Data

(60) Provisional application No. 60/076,137, filed on Feb. 27, 1998.

(51) Int. Cl.[7] .............................................. G01N 33/20

(52) U.S. Cl. ........................... 436/83; 436/73; 436/161; 436/175; 436/178

(58) Field of Search ........................... 436/83, 73, 161, 436/175, 178

(56) References Cited

U.S. PATENT DOCUMENTS 4,322,542 A   3/1982  Abbott
4,333,847 A * 6/1982  Tran et al. .................... 588/12

FOREIGN PATENT DOCUMENTS

RU   2024848    12/1994
SU   1571497    6/1990

OTHER PUBLICATIONS

Koschcheeva, I. Ya.; Velyukhanova, T. K.; Khar'kov, N. Ye.; Zhukov, S. R.; Kudinova, T. F.;"Sequential elution of different forms of heavy metals from polluted soils", Pochvovedenie (1991), (9), pp. 148–154.*

Girard, L.; Hubert, J."Speciation of chromium (VI) and total chromium determination in welding dust samples by flow–injection analysis coupled to atomic–absorption spectromerty", Talanta, (1996), 43 (11), pp. 1965–1974.*

(List continued on next page.)

*Primary Examiner*—Jeffrey Snay
*Assistant Examiner*—Yelena Gakh
(74) *Attorney, Agent, or Firm*—Needle & Rosenberg, P.C.

(57) ABSTRACT

A method for the determination of hexavalent chromium ($Cr^{VI}$) in environmental and industrial hygiene samples is provided. Based on the chemical properties of chromium species in aqueous solutions, a simple, fast, sensitive, and economical field method has been developed and evaluated for the determination of hexavalent chromium ($Cr^{VI}$). Using ultrasonic extraction in combination with a strong anion exchange solid phase extraction (SAE-SPE) technique, the filtration, preconcentration, and isolation of $Cr^{VI}$ in the presence of other chromium species and interferents was achieved. The method generally involves: (1) ultrasonication in basic buffer solution to extract $Cr^{VI}$ from environmental matrices; (2) strong anionic exchange solid phase extraction to separate $Cr^{VI}$ from other chromium species and potential interferents; (3) acidification of the eluate containing the $Cr^{VI}$ ions; (4) complexation of $Cr^{VI}$ with a complexing agent to form a soluble, colored $Cr^{VI}$-complex; and (5) spectrophotometric determination of the colored $Cr^{VI}$-complex. Preferably, the ultrasonication step is carried out in the presence of a slightly basic ammonium buffer and the complexing agent is 1,5-diphenylcarbazide.

19 Claims, 2 Drawing Sheets

OTHER PUBLICATIONS

Wang, Jin; Ashley, Kevin; Marlow, David; England, Ellen,; Carlton, Gary" Field Method for determination of hexavalent chromium by ultrasonication and strong anion–exchange solid–phase extraction" Anal. Chem., (1999), 71 (5), pp. 1027–1032.*

Ndung'u, Kuria; Djane, Nii–Kotey; Malcus, Frederik; Mathiasson, Lennart "Ultrasonic extraction of hexavalent chromium in solid samples . . . ", Analyst (Cambridge, U.K.), (1999), 124 (9), pp. 1367–1372.*

Marlow, David; Wang, Jin; Wise, T. J.;Ashley, Kevin; "Field test of a portable method for the determination of hexavalent chromium in workplace air", Am. Lab. (Shelton, Conn.) (2000), 32 (15), pp. 26–28.*

Wang et al. "Determination of Hexavalent Chromium in Industrial Hygiene Samples Using Ultrasonic Extraction and Flow" Analyst, Nov. 1997, vol. 122, pp. 1307–1312.

* cited by examiner

METHOD FOR THE DETERMINATION OF HEXAVALENT CHROMIUM USING ULTRASONICATION AND STRONG ANION EXCHANGE SOLID PHASE EXTRACTION

This application is a 35 U.S.C. §371 national phase application from and which claims priority to, international application PCT/US99/04200, filed Feb. 25, 1999, which claims Benefit of U.S. Provisional Application Ser. No. 60/076,137, filed Feb. 27, 1998, which applications are hereby incorporated herein in their entirety.

FIELD OF THE INVENTION

This invention relates to a method for the determination of hexavalent chromium ($Cr^{VI}$). More specifically, the present invention relates to a simple, fast, sensitive, and economical method for the determination of $Cr^{VI}$ which is especially adapted for environmental and work place samples (including solid and air samples). The present method can be used in both laboratory and field analysis.

BACKGROUND OF THE INVENTION

Chromium exists primarily in two valence states, trivalent ($Cr^{III}$) and hexavalent ($Cr^{VI}$). The trivalent state is relatively non-toxic, and is an essential nutrient in the human diet. On the other hand, $Cr^{VI}$ has been shown to be a human respiratory carcinogen in epidemiological studies of workplace exposures, and has been classified by the U.S. Environmental Protection Agency (EPA) as a Group A inhalation carcinogen. Hence, analytical methods are desired which can be used to easily speciate chromium so that human exposures to $Cr^{VI}$ can be monitored and, thus, better controlled.

Workplace exposure to $Cr^{VI}$ has been associated with a number of industrial sources, such as metal plating, spray painting, welding, tanning, and abrasive blasting operations. Environmental sources of $Cr^{VI}$ include, for example, deteriorated or disturbed chromate-containing paint, combustion sources such as automobiles and incinerators, and fugitive dusts from contaminated solid. Because of the desire to accurately measure $Cr^{VI}$ at low levels, the development of analytical methods for the determination of $Cr^{VI}$ has been a subject of significant interest in occupational and environmental health.

Chromium has been detected using atomic absorption spectrometry (Mehra et al., Talanta, 1989, 36(9), 889; Fong et al., Spectrosc. Lett. 1991, 24, 931), atomic absorption spectrometry (Jarvis et al., Analyst, 1987, 122, 19; Arar et al., Environ. Sci. Technol., 1992, 29, 1944); atomic emission spectrometry (Boumans, Line Coincidence Tables for Inductively Coupled Plasma Atomic Emission Spectrometry, Oxford University Press, Oxford, 2nd ed., 1984; Giglio et al., Anal. Chim. Acta, 1991, 254, 109; Roychowdhury et al., Anal. Chem., 1990, 62, 484), X-ray fluorescence (Arber et al., Analyst, 1988, 113, 779), charged-particle X-ray emission spectrometry and neutron activation analysis. National Institute for Occupational Safety and Health (NIOSH) Methods 7024 and 7300 (NIOSH Manual of Analytical Methods, Eller & Cassinelli (eds)., National Institute for Occupational Safety and Health, Cincinnati, Ohio, 4th ed, 1994) use atomic absorption spectrometry and atomic absorption spectrometry, respectively, for the determination of chromium in workplace air samples. These methods, however, generally determine only total. Moreover, these methods generally involve expensive and complex instrumentation and are not, therefore, generally suitable for monitoring directly in the field.

Spectrophotometric and colorimetric methods have been developed for the determination of $Cr^{VI}$. See, for example, Alvarez et al., Talanta, 1989, 36(9), 919; Haukka, analyst, 1991, 116, 1055; Abel et al., Am. Ind. Hyg. Assoc. J., 1974, 35, 229. The most prevalent colorimetric method uses the selective reaction of $Cr^{VI}$ with 1,5-diphenylcarbazide (DPC) under acidic conditions to yield a red-violet $Cr^{VI}$-diphenylcarbazone complex. A variation of this colorimetric method is used in NIOSH method 7600 (NIOSH Manual of Analytical Methods, Eller & Cassinelli (eds.), National Institute for Occupational Safety and Health, Cincinnati, Ohio, 4th ed, 1994) where alkaline extraction is used to help stabilize the $Cr^{VI}$ species. Stripping voltammetry (Wang et al., Analyst, 1992, 117, 1913; Elleouet et al., Anal. Chim. Acta, 1992, 257, 301) and ion chromatographic assays (Powell et al., Anal. Chem., 1995, 67, 2474; Vercoutere et al., Mikrochim. Acta., 1996, 123, 109; Molina et al., Am. Ind. Hyg. Associ. J., 1987, 48, 830; ASTM D 5281–92, "Standard Test Method for Collection and Analysis of Hexavalent Chromium," in Annual Books of ASTM Standards, American Society for Testing and Materials, vol. 11.01, Philadelphia, Pa., 1992; U.S. Environmental Agency, Method 218.6. Determination of Dissolved Hexavalent Chromium in Drinking Water, Groundwater and Industrial Waste Water Effects by Ion Chromatography, EPA Office of Research and Development, Cincinnati, Ohio, 1990; U.S. Environmental Agency, Method 3060A, "Alkaline Digestion for Hexavalent Chromium" in Test Methods for Evaluating Solid Wastes, EPA, Washington, D.C., 1995) have also been used to determine $Cr^{VI}$ in various samples. Many of these techniques are limited to laboratory-based analysis and cannot, therefore, be used in field monitoring and/or real-time evaluations.

Over the past decade, solid phase extraction (SPE) has been established in the analytical chemistry laboratory and has become increasingly popular. The use of SPE for the separation and preconcentration of trace polar or non-polar target analytes has been widely investigated, and the advantages of such a technique over a conventional liquid-liquid extraction, coprecipitation, electrochemical deposition and evaporation have been well documented. See, for example, Masque et al., Analyst, 1997, 122, 425–428; Corcla et al., Environ. Sci. Technol., 1994, 28, 850–858; Shahteri et al., J. Chromatogr., 1995, 697, 131–136. Some of the advantages of SPE over classical analytical methods include: (1) efficiency and simplicity; (2) solvent minimization and enhanced safety with respect to hazardous samples; (3) high preconcentration factors; (4) good recoveries; (5) flexibility; and (6) low cost.

Both off-line and on-line SPE methodologies have been employed for the preseparation and preconcentration of a variety of analytes. Off-line SPE methodologies involve the use of packing materials that may contain functional groups of different polarity such as $C_8$ or $C_{18}$ bonded silica phases (Falco et al., Analyst, 1997, 122, 673–677). With on-line SPE, followed by high pressure liquid chromatography, a critical parameter is the selection of an adequate precolumn in order to avoid band broadening of the first eluded peaks, and to allow for the percolation of large sample volumes (Kiss et al., J. Chromatogr., 1996, 725, 261–272). Numerous solid-phase extractants, such as pure or modified silica, alumina, magnesia, activated carbon, polyurethane, and cellulose and its derivatives, have been used in SPD techniques. Consequently, solid phase extraction has largely replaced classical liquid-liquid extraction in the analytical laboratory.

More recently, innovative new cartridges for SPE, such as reversed-phase and ion-exchange of target analytes in a single resin, are being developed and many are commercially available. These resins cartridges allow for sorption of the analyte of interest while removing non-sorbed interferents, with fast, quantitative adsorption and high elution capacities. These cartridges can improve the overall specificity and sensitivity of trace analysis. Furthermore, the use of commercially available, low cost vacuum manifolds for SPE allows for up to, and even greater than, 24 samples to be processed simultaneously. Complete automation of procedures based on SPE are also available with commercial instrumentation. Despite these advantages, there have been relatively few applications of SPE to inorganic materials, including heavy metals.

Ultrasonic extraction (UE) for the purpose of dissolving target heavy metal analytes in environmental samples is also a technique that has not been used extensively, although it offers great promise (Lugue de Castro et al., Trends Anal. Chem., 1997, 16, 16–24). UE has been demonstrated to perform well for the quantitative dissolution of several heavy metals in a variety of environmental matrices (Harper et al., Anal. Chem., 1983, 55, 1553–1557; Sanchez et al., Analysis, 1994, 22, 222–225; Ashley, Electroanalysis, 1995, 7, 1189–1192z), including hexavalent chromium (James et al., Environ. Sci. Technol., 1995, 29, 2377–2381).

Nonetheless, there remains a need for a simple, reliable, fast, inexpensive, and field-based method for the detection of $Cr^{VI}$ in environmental and workplace samples. This invention, combining the use of ultrasonic extraction and strong anion exchange solid phase extraction, provides such a method. This method provides a novel and effective approach for the on-side determination of $Cr^{VI}$ in environmental and workplace samples.

SUMMARY OF THE INVENTION

This invention relates to a method for the determination of hexavalent chromium ($Cr^{VI}$). Based on the chemical properties of chromium species in aqueous solutions, a simple, fast, sensitive, and economical field method has been developed and evaluated for the determination of hexavalent chromium ($Cr^{VI}$) in environmental and workplace air samples. By means of ultrasonic extraction in combination with a strong anion exchange solid phase extraction (SAE-SPE) technique, the filtration, preconcentration, and isolation of $Cr^{VI}$ in the presence of other chromium species and interferents was achieved. The method generally involves: (1) ultrasonic in basic buffer solution to extract $Cr^{VI}$ from environmental matrices; (2) strong anion exchange solid phase extraction to separate $Cr^{VI}$ from other chromium species and potential interferents; (3) acidification of the eluate containing the $Cr^{VI}$ ions; (4) complexation of $Cr^{VI}$ with a complexing agent to form a soluble, colored $Cr^{VI}$-complex; and (5) spectrophotometric determination of the colored $Cr^{VI}$-complex. Preferably, the ultrasonication step is carried out in the presence of a slightly basic ammonium buffer and the complexing agent is 1,5-diphenylcarbazide. This present method can effect the extraction of both soluble ($K_2CrO_4$) and insoluble ($K_2CrO_4$) forms of $Cr^{VI}$ without inducing $Cr^{III}$ ($Cr_2O_3$) oxidation of $Cr^{VI}$ reduction. The method allows for the dissolution and purification of $Cr^{VI}$ from environmental and workplace air sample matrices for up to 24 samples (or even higher numbers) simultaneously in less than about 20 minutes (excluding the ultrasonic extraction time). The present method is simple, fast, quantitative, and sufficiently sensitive for the determination of occupational exposures of $Cr^{VI}$. The method is especially applicable for on-site monitoring of $Cr^{VI}$ in environmental and industrial hygiene samples, including both solid samples (e.g., soil, paint chips, dust, solid residues, and the like) and air samples.

One objective of the present invention is to provide a method for the detection of $Cr^{VI}$ in a sample, said method comprising:

(1) ultrasonic extraction of $Cr^{VI}$ from the sample utilizing a first buffer solution (i.e., the ultrasonic buffer) having a slightly basic pH, whereby the pH of the first buffer solution is such that neither significant $Cr^{III}$ oxidation nor $Cr^{VI}$ reduction occurs;

(2) separation of the $Cr^{VI}$ in the ultrasonic extractant from step (1) from any $Cr^{III}$ or other interferents that might be present in the sample by passage of the ultrasonic extractant through a strong anion exchange solid phase extraction media;

(3) elution of the $Cr^{VI}$ from the media with a second buffer solution (i.e., the elution buffer) having a slightly basic pH;

(4) acidification of the eluate containing the $Cr^{VI}$; and (5) addition of a complexing agent to the acidified eluate to form a colored $Cr^{IV}$-complex if $Cr^{VI}$ is present in the sample. The ultrasonication step employed to liberate $Cr^{VI}$ from the sample matrix is preferably carried out using a slightly basic ammonium buffer and the complexing agent is preferably, 1,5-diphenylcarbazide. Preferably, the amount of $Cr^{VI}$ present in the sample is determined using any appropriate technique. More preferably, the amount of $Cr^{VI}$ present in the sample is determined using a simple and direct spectrophotometric procedure which can be used in the field or on-site.

Another objective of the present invention is to provide a method for the quantitative detection of $Cr^{VI}$ in a sample suspected of containing $Cr^{VI}$, said method comprising:

(1) ultrasonic extraction of $Cr^{VI}$ from the sample utilizing a first ammonium buffer solution (i.e., the ultrasonic buffer) having a slightly basic pH, whereby the pH of the ammonium buffer solution is such that neither significant $Cr^{III}$ oxidation nor $Cr^{VI}$ reduction occurs;

(2) separation of the $Cr^{VI}$ in the ultrasonic extractant from step (1) from any $Cr^{III}$ or other interferents that might be present in the sample by passage of the ultrasonic extractant through a strong anion exchange solid phase extraction media;

(3) elution of the $Cr^{VI}$ from the media with a second ammonium buffer solution (i.e., the elution buffer);

(4) acidification of the eluate containing $Cr^{VI}$;

(5) addition of 1,5-diphenylcarbazide to the acidified eluate to form a colored $Cr^{VI}$-1,5-diphenylcarbazone complex if $Cr^{VI}$ is present in the sample; and (6) subjecting the $Cr^{VI}$-1,5-diphenylcarbazone complex, if present, from step (5) to a spectrophotometric analysis in order to determine the amount of $Cr^{VI}$ present in the sample.

These and other objectives and advantages of the present invention will be apparent to those of ordinary skill in the art upon consideration of the present specification.

DESCRIPTION OF THE PREFERRED EMBODIMENTS

Figure 1:
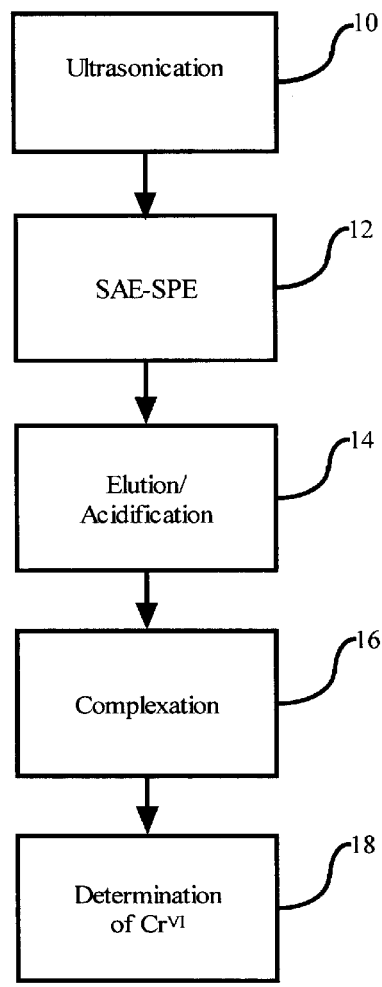
FIG. 1 is a flowchart illustrating the general procedures utilized in the present method.

This invention provides a simple, fast, sensitive, and economical field method for the determination of hexavalent chromium ($Cr^{VI}$), especially in environmental samples and workplace air samples. The present method combines ultrasonic extraction and a strong anion exchange solid phase extraction (SAE-SPE) technique to allow the filtration, preconcentration, and isolation of $Cr^{VI}$ in the presence of other chromium species and interferents. The present method is generally illustrated in FIG. 1. In the first step, ultrasonication 10 is used to extract $Cr^{VI}$ in the sample from its environmental matrix. After ultrasonic extraction, a strong anion exchange solid phase extraction (SAE-SPE) step 12, preferably using a column or cartridge system, is used to separate $Cr^{VI}$ from other chromium species and potential interferents. The $Cr^{VI}$ species retained on the column or cartridge containing the solid absorbing system to allow separation from $Cr^{III}$ species and other potential interferents in the sample. The $Cr^{III}$ and other potential interferents pass through the column to effect the separation. The $Cr^{VI}$ species are then eluted from the column or cartridge and collected. The eluant containing the $Cr^{VI}$ species is then acidified in step 14. The acidified eluant is then treated with a complexing agent in step 16 to form a colored $Cr^{VI}$-complex which can be detected in step 18 using any appropriate means (e.g., visual, spectroscopic, or similar methods).

Figure 2:
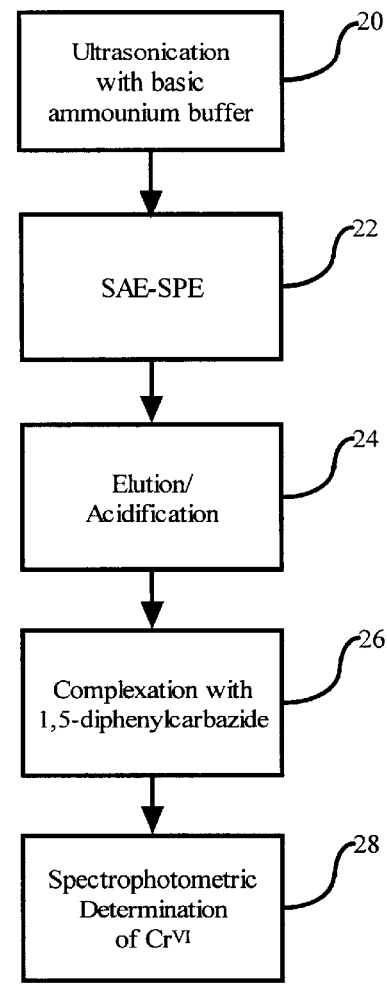
FIG. 2 is a flowchart illustrating one preferred embodiment of the present invention.

An especially preferred embodiment of the present invention is illustrated in FIG. 2. This preferred embodiment involves a first ultrasonication step 20 using a slightly basic ammonium buffer solution to extract $Cr^{VI}$ from the environmental matrices at a pH to avoid significant $Cr^{III}$ oxidation and/or $Cr^{VI}$ reduction. A strong anion exchange solid phase extraction (SAE-SPE) step 22 is then used to separate $Cr^{VI}$ from other chromium species and potential interferents. Step 22 is preferably carried out using a column or cartridge containing pre-packed strong anion exchange material. $Cr^{VI}$ is then removed from the column or cartridge preferably using, for example, a slightly basic ammonium solution. The collected eluant containing $Cr^{VI}$ is then acidified in step 24. An effective amount of 1,5-diphenylcarbazide is added to the eluant containing $Cr^{VI}$ in step 26 to form a soluble, colored $Cr^{VI}$-1,5-diphenylcarbazone complex. In the last step 28, the amount of $Cr^{VI}$ is determined using a suitable spectrophotometric technique.

The ultrasonication step employed to liberate $Cr^{VI}$ from the sample matrix should be carried out using a slightly basic aqueous buffer solution so as to reduce the levels of $Cr^{III}$ oxidation and $Cr^{VI}$ reduction to low (i.e., insignificant) levels. Generally, the pH of buffered solution used in the ultrasonic extraction step is in the range of about 7.2 to 9.0, preferably in the range of about 7.5 to 8.5, and most preferably about 8.0. Preferably the ultrasonic solution is a buffered aqueous ammonium solution containing between about 0.02 M to 0.2 M $(NH_4)_2SO_4$ and about 0.02 M to 0.2 M $NH_4OH$, even more preferably about 0.025 M to 0.1 M $(NH_4)_2SO_4$ and about 0.025 M to 0.1 M $NH_4OH$, and most preferably about 0.05 M $(NH_4)_2SO_4$ and about 0.05 M $NH_4OH$ and a pH of about 8.0. Other alkaline buffers (e.g., tris(hydroxymethyl)aminomethane hydrochloride (Tris-HCl) where ammonium or ammonium hydroxide is used to obtain the desired basic pH; ammonium carbonate; generally basic buffers containing $NH_4^+$ cations) can also be used. The ultrasonic extraction step can be carried out using any conventional ultrasonic bath. Ultrasonification for about 15 to 60 minutes at about room temperature or slightly elevated temperatures should be sufficient to release the $Cr^{VI}$ contained in the sample. Preferably, the ultrasonification is carried out a temperatures less than about 40° C. in order to minimize oxidation and reduction reactions. Routine experimentation can easily be carried out to determine the optimum ultrasonification conditions for any particular sample. After the ultrasonication step, the sample can be filtered if desired to remove solid material before application to the strong anion exchange resin.

Once the $Cr^{VI}$ species has been liberated by ultrasonification, the sample is treated using a strong anion exchange resin to separate the $Cr^{VI}$ species from other chromium species as well as other potential interferents. The $Cr^{VI}$ which is retained on the strong anion exchange resin can be eluted using a slightly basic aqueous buffer system. Suitable strong anion exchange resins include, for example, styrene-divinylbenzene polymer resins to which tertiary ammonium groups have been bound (e.g., Dowex 1-X8 from Fluka Chemical, Ronkonkoma, N.Y.) and quaternary amine bonded silica with $Cl^-$ as the counter ion (Supelco, Inc., Bellefontaine, Pa.). Other strong anion exchange resins can be used so long as they allow separation of $Cr^{VI}$ from $Cr^{III}$ and other potential interferents. Generally, cartridges pre-packaged with the strong anion exchange resins are much easier to use and are, therefore, preferred. Strong anion exchange resins with a capacity of about 0.1 to about 2.0 meq/g are generally preferred. The strong anion exchange resins are conditioned or activated according to known procedures; such procedures are normally supplied by the resin manufacturer.

The general procedure for the preferred SPE-SAE procedure will now be detailed using a quaternary amine bonded silica resin ($Cl^-$ counter ion) as the strong anion exchange media. A suitable solid-phase extractor (from, for example, Supelco, Inc., Bellefontaine, Pa.) can be attached to an appropriate small vacuum pump via a metering valve in order to assist passage of the sample and other reagents through the resin. A cartridge (3 ml) containing about 500 mg quaternary amine bonded silica sorbent with $Cl^-$ as the counter ion (capacity about 0.2 meq/g) is placed in the solid-phase extractor and then conditioned with about 3 ml of deionized water to activate the functional groups in order to allow the $Cr^{VI}$ to be absorbed on the resin. The sample (generally about 1 to 5 ml) obtained from the sonification extraction step is then loaded on the cartridge and passed through the resin at a flow rate of about 1 ml/min to about 2 ml/min. The $Cr^{VI}$ remains on the resin. After washing the cartridge with deionized water (generally about 1 to 5 ml), the $Cr^{VI}$ is removed from the cartridge with a slightly basic buffer solution (generally about 4 to 10 ml in 1 to 3 portions) and the elutant containing the $Cr^{VI}$ is collected. Washing the column with water prior to removal of the $Cr^{VI}$ helps to remove potentially interfering materials. Of course, as one of ordinary skill in the art will realize, larger or smaller cartridges or columns will generally required larger or smaller amounts, respectively, of the relevant reagents.

The buffer system used to elute the $Cr^{VI}$ from the strong anion exchange resin may be the same or different from that used in the ultrasonification step. It should, however, be slightly basic to avoid $Cr^{VI}$ reduction. It is generally preferred that a buffered aqueous ammonium solution containing between about 0.25 M to 1.0 M $(NH_4)_2SO_4$ and about 0.25 M to 1.0 M $NH_4OH$ is used as the eluting buffer. More preferably, the eluting buffer solution contains about 0.5 M $(NH_4)_2SO_4$ and about 0.5 M $NH_4OH$ at a pH of about 8.0. Generally, the eluting buffer system is more concentrated (preferably by a factor of about 10) than the ultrasonic buffer system. Other alkaline buffers (e.g., tris(hydroxymethyl) aminomethane hydrochloride (Tris-HCl) where ammonium or ammonium hydroxide is used to obtain the desired basic pH; ammonium carbonate; generally basic buffers containing $NH_4^+$ cations) can also be used.

After elution from the SAE column or cartridge, the $Cr^{VI}$-containing element is acidified using suitable acids (e.g., sulfuric acid, hydrochloric acid, acetic acid, and the like). Generally the pH is not critical so long as the eluant is acidic. After acidification, the complexing agent is added to form a detectable $Cr^{VI}$-complex. The complexing agent is added in excess in order to maximize the amount of $Cr^{VI}$-complex formed. In other words, the amount of complexing agent should be sufficient to complex with essentially all of the $Cr^{VI}$ present in the sample. Examples of suitable complexing agents include 1,5-diphenylcarbazide, 2-(5-bromo-2-pyridylazo-5-(diphenylamino)phenol, L-penicillamine, 2-mercaptonicotinic acid, and the like. 1,5-Diphenylcarbazide is the preferred complexing agent. The $Cr^{VI}$-1,5-diphenylcarbazone complex is red-violet with an absorbance maxima at about 520–540 nm. Generally color formation occurs within a few seconds and is stable for several hours. Nonetheless, it is generally preferred that the detection step be undertaken shortly after complex formation. The dynamic range of the chromium-diphenylcarbazone complex was generally linear from about 10 μg/l to about 5 mg/l ($R^2$=0.99997) using spectrophotometric determination. Selectivity was also excellent since typical interferences, including $Cr^{III}$, $Fe^{III}$, and $Cu^{III}$, are essentially eliminated in the SAE procedure.

Quantitative or qualitative detection of the resulting $Cr^{VI}$-complex can be any suitable means. For example, the development of the colored $Cr^{VI}$-complex itself visually indicates the presence of $Cr^{VI}$ in the sample. Preferably UV/VIS-based spectrophotometric detection methods are preferred for quantitative colorimetric measurement. A standard cataloging spectrophotometer, especially one adapted for field operation, is generally preferred so as to provide a portable, field-adapted detection method. For detection of $Cr^{VI}$ using the 1,5-diphenylcarbazide complexing agent, a spectrophotometer operating about 540 nm is preferred; this wavelength provides maximum sensitivity and generally eliminates interference of excess (i.e., uncomplexed) 1,5-diphenylcarbazide complexing reagent.

The present method may be either manual, semi-automated, or fully automated. Manual or semi-automated analysis and detection techniques might be used, for example, for screening or spot-checking a workplace environment to determine if $Cr^{VI}$ exposure is likely and if further, more extensive, sampling is necessary. Generally, automated techniques wherein multiple samples can be evaluated at the same time are preferred. For example, a flow injection analysis system as described in Wang et al. (Analyst, 1997, 12, 1307–1312, which is hereby incorporated by reference) can be employed. Such a system, employing a pump and an automated operating under low pressure and computer control can be used to automate the precise manipulation of microliter amounts of samples and deliver the products to a flow-through colorimetric detector for the detection of $Cr^{VI}$. In addition, commercially available, low cost vacuum manifolds for SPE can allow multiple samples to be run; generally, 24 samples (or more with appropriate modifications) at a time can easily be evaluated. Commercial instrumentation is also available by which the SPE process can be automated. Thus, the present method can provide a low cost, simple, fast, quantitative, and sensitive method for the determination of occupational exposure of $Cr^{VI}$. This method is ideally suited for on-site monitoring of $Cr^{VI}$ in environmental and industrial hygiene applications.

EXAMPLES

The following examples are provided to illustrate the invention and not to limit the invention. All references cited in the present specification are hereby incorporated by reference.

Instrumentation and Reagents. Ultrasonic extraction was performed using a Sonicor 115V, 60 Hz laboratory sonicator (Sonicor Instruments, Farningdale, N.Y., USA). The solid-phase extractor was obtained from Supelco, Inc. (Bellefontaine, Pa., USA), and was attached to a small vacuum pump via a pressure metering valve. The strong anion exchange cartridge used in the solid phase extraction contained 500 mg quaternary amine bonded silica sorbent with $Cl^-$ as counter ion for storing anion exchange (capacity 0.2 meg/g); the tube size was 3 ml. These pre-packaged cartridges were obtained from Supelco, Inc., Bellefontaine, Pa. A portable cataloging spectrophotometer (HACH DR/2010, HACH Company, Loveland, Colo.) was used for spectrophotometric measurement.

Hexavalent and trivalent chromium standards, ammonium sulfate, ammonium hydroxide, 1,5-diphenylcarbazide (DPC), chromium oxide ($Cr_2O_3$), potassium chromate ($K_2CrO_4$), hydrochloric acid, sulfuric acid, and nitric acid were all reagent grade from Aldrich (Milwaukee, Wis.). Tris(hydroxymethyl)aminomethane hydrochloride (Tris-HCl) was from Sigma, Inc. (St. Lous, Mo.) Lead chromate $PbCrO_4$) as from Fisher Scientific (Elizabeth, N.J.). Chromium-containing reference materials were used as supplied: (1) paint chips—US EPA Certified Reference Material (CRM) 013-050, Laramie, Wyo.; (2) coal fly ash—National Institute of Standards and Technology (NIST) Standard Reference Material (SRM) 1633a, Gaithersburg, Md.; and (3) welding dust loaded on glass fiber filters—Institute for Reference Materials and Measurements (IRMM) CRM 545) from the European Commission (IRMM, Geel, Belgium). For air samples, preloaded filter cassettes containing mixed cellulose ester membrane filters (0.8μ pore size, 0.37 mm diameter) were obtained from SKC Inc. (Eighty Four, Pa.).

Solid-Phase Extraction Procedures. Solid-phase extraction (SPE) was performed with the aid of an extractor and a strong anion exchange (SAE) cartridge. The SAE cartridge contained a silica sorbent to which a quaternary amine was bound; chloride ion functional as the counter ion. Cartridges were conditioned with 3 ml of deionized water, which activated the functional groups on the sorbent, allowing for binding of $Cr^{VI}$ onto the SAE sorbent. Subsequently, a 3 ml aliquot of sample solution was loaded on the SAE cartridge. After sample loading, the cartridge was rinsed with 3 ml of deionized water to remove potential interferents. Then, elution of the $Cr^{VI}$ concentrated on the SAE cartridge was performed with 9 ml of 0.5 M ammonium sulfate buffer solution in three 3 ml fractions.

Sample Collection. Workplace air samples were collected from aircraft painting operations at U.S. Air Force bases using 0.8 micron, 37-mm cellulose ester membrane filters. Samples were obtained from different work practices including priming, sanding, alodining, cutting, and grinding. The samples were transported to the laboratory immediately after collection, and stored in a refrigerator at 4° C. until prepared for analysis. Environmental samples were collected using standard techniques.

General Procedure for Environmental and Workplace Air Samples. Samples were placed into 15 ml plastic centrifuge tubes. Sample preparation consisted of adding 10 ml of 0.05 M $(NH_4)SO_4$ and 0.05 M $NH_4OH$ (pH 8) buffer solution to the sample followed by sonication in an ultrasonic bath for 30 minutes at ambient temperature (<40° C.). After ultrasonication, a 3 ml aliquot of the supernatant was loaded onto a strong anion exchange cartridge. The $Cr^{VI}$ was eluted with 9 ml 0.5 M $(NH_4)SO_4$ and 0.1 M $NH_4OH$ (pH 8) buffer solution in three 3 ml fractions at a flow rate of 2 ml/min. After isolation and purification, the eluate was acidified with 100 µl 37% HCl solution. This was followed by mixing with 2 ml of 20 mM 1,5-diphenylcarbazide complexing reagent. The reaction of 1,5-diphenylcarbazide with $Cr^{VI}$ is completed in a few seconds and the color of the complex can be stable for at least 8 hours. If analysis is not to be completed shortly after complex formation, it is preferred that they be stored at refrigerated temperatures.

Detection of Hexavalent Chromium. Quantification of hexavalent chromium was done by external standard or standard addition methods with the spectrophotometer set at 540 nm. For the air samples, a standard addition calibration was used. Blank filters and quality control/quality assurance samples (standard solutions of known hexavalent chromium concentration) were analyzed at a minimum frequency of one per twenty experimental samples.

Example 1

Absorption Capacity Studies

Absorption capacities were determined using spiked $Cr^{VI}$ solutions produced by dissolving $K_2CrO_4$ in 0.02 M, 0.05 M, and 0.5 M ammonium sulfate and ammonium hydroxide buffer solutions (pH 8). Four different $Cr^{VI}$ spiked solutions (1.0 M, 2.0 mM, 4.0 mM, and 8.0 mM) were prepared and loaded onto the cartridge, eluted, and analyzed in triplicate to establish the reproducibility of the procedure. Breakthrough of the analyte was determined by analysis of the solution that passed through the SAE cartridge after loading of sample aliquots.

Figure 3:
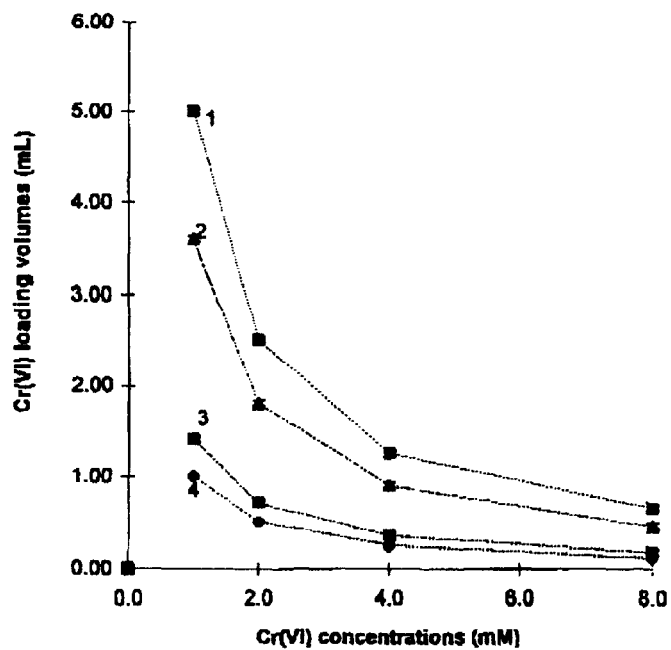
FIG. 3 illustrates the breakthrough of $Cr^{VI}$ using a strong anion exchange solid phase extraction column. Curve 1 uses an elution solution of 0.02 M ammonia sulfate and 0.02 M ammonia hydroxide buffer; Curve 2 uses an elution solution of 0.05 M ammonia sulfate and 0.05 M ammonia hydroxide buffer; Curve 3 uses an elution solution of 0.5 M ammonia sulfate and 0.5 M ammonia hydroxide buffer; Curve 4 uses an elution solution of 1.0 M ammonia sulfate and 1.0 M ammonia hydroxide buffer.

The results are shown in FIG. 3 which shows that the initial breakthrough that was observed at various $Cr^{VI}$ loading volumes with the flow rate controlled at 2 ml/min. Similar results (not shown) were obtained with matrix spikes of cellulose ester filters. The adsorption capacities of SAE cartridges changed with increasing concentration of the ammonium sulfate and ammonium hydroxide buffer in the sample solutions (FIG. 3). The adsorption capacity of SAE cartridges for $Cr^{VI}$ decreased more than threefold when the concentration of ammonium sulfate and ammonium hydroxide buffer solution was changed from 0.02 M (FIG. 3, Curve 1) to 1.0 (FIG. 3, Curve 4) at the same controlled flow rate of 2 ml/min. The adsorption capacities of SAE cartridges were also related to sample loading flow rates. At a high flow rate of loading (e.g., 4–5 ml/min), the breakthrough of the $Cr^{VI}$ was more evident that was observed at a lower loading flow rate (e.g., 1 ml/min) under the same other experimental parameters. The percentage breakthrough increased with increased loading speed, and an optimum flow rate of about 2 ml/min was arrived at by trial and error. Generally, the throughput flow rate is an important function of SPE. Loading flow rates are often more critical to optimizing recoveries than are the conditioning and rinse flow rates. In the conditioning step, there is nothing bound to the cartridge, and the flow rate can sometimes be increased without a loss of recovery. Flow rates may also be increased in the rinse step depending upon the banding mechanism and the sorbent/adsorbate chemistry. These trials (FIG. 3) have demonstrated that reducing the concentrations of ammonium sulfate and ammonium hydroxide buffer in sample solution can improve the adsorption capacity and minimize cartridge breakthrough.

When air samples containing chromium were tested to study SAE cartridge breakthrough, they were treated in an identical manner as spiked $Cr^{VI}$ solutions in order to evaluate the effects of ammonium sulfate and ammonium hydroxide buffer solution (pH 8) used in the extraction procedure. In these trials, the samples were treated with ultrasonication for 30 min at ambient temperature (<40° C. bath temperature) in ammonium sulfate buffer solution. The results demonstrated no significant breakthrough of $Cr^{VI}$ when an ammonium sulfate and ammonium hydroxide buffer solution ($\leq 0.05$ M) was used to extract $Cr^{VI}$ from samples via sonication.

Example 2

Elution Studies

Ammonium sulfate and ammonium hydroxide buffer was used as the elution buffer solution. To obtain optimum recoveries, spiked $Cr^{VI}$ solutions of four levels (10.0 µl, 20.0 µl, 40.0 µl, 80.0 µl) were eluted using different number of fractions of 0.5 M ammonium sulfate and ammonium hydroxide buffer solution (pH 8). Eluting power was investigated for five levels of $Cr^{VI}$ solutions (50.0 µg, 100.0 µg, 200.0 µg, 400.0 µg, 600.0 µg) at various flow rates. In each experiment, only one parameter was changed at a time. When elution flow rate is considered, it should not be too fast, since the analyte of interest may not have enough time to desorb from the cartridge. Nor should the flow rate be too slow, or sample preparation may be too time-consuming. As those skilled in the art will understand, the optimum flow-rates can be determined experimentally for a given experimental setup.

Figure 4:
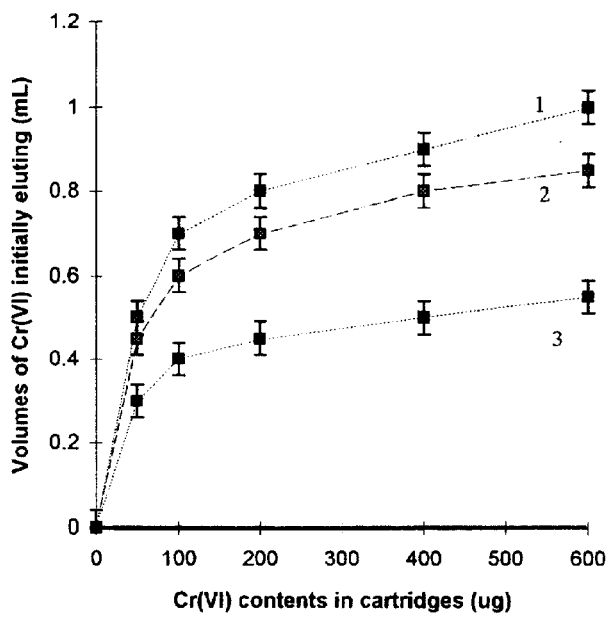
FIG. 4 illustrates the elution of varying concentration of $Cr^{VI}$ using a strong anion exchange solid phase extraction column with varying. Curve 1 uses an elution solution of 0.5 M ammonia sulfate and 0.5 M ammonia hydroxide buffer; Curve 2 uses an elution solution of 1.0 M ammonia sulfate and 1.0 M ammonia hydroxide buffer; Curve 3 uses an elution solution of 2.0 M ammonia sulfate and 2.0 M ammonia hydroxide buffer.

To evaluate the effect of ion exchange due to the elution power, eluting solutions of 0.5 M, 1.0 M, or 2.0 M ammonium sulfate and ammonium hydroxide buffer solutions (pH 8) were tested by eluting spiked $Cr^{VI}$ solutions at 5 levels (50 µg, 100 µg, 200 µg, 400 µg, 600 µg). The results are shown in FIG. 4. The $Cr^{VI}$ started to initially elute at various volumes of buffer solution, corresponding to different contents of $Cr^{VI}$ loaded the cartridges. Increasing the concentrations of the ammonium sulfate and ammonium hydroxide in elution solution from 0.5 M (FIG. 4, Curve 1) to 2.0 M (FIG. 4, Curve 3) did not significantly change the $Cr^{VI}$ eluting time. By eluting with 0.5 M ammonium sulfate and ammonium hydroxide buffer solution, the $Cr^{VI}$ at all 5 levels started to elute all flow rates lower than 1 ml/min, which is lower than the generally used flow rate of 2 ml/min. Therefore, by considering the adsorption capacity of SAE cartridges (FIG. 4, Curve 1), 0.5 M ammonium sulfate and ammonium hydroxide buffer solution was determined to perform best as an elution buffer solution in these experiments with the particular experimental setup employed.

Table I shows the recoveries of $Cr^{VI}$ obtained from spiked $Cr^{VI}$ solutions at 4 levels (10.0 μg, 20.0 μg, 40.0 μg, 80.0 μg) using varying number of eluting fractions (each fraction consisted of 3 ml of 0.5 M $(NH_4)_2SO_4$ and 0.1 M $NH_4OH$ (pH 8) buffer).

TABLE I

| Spiked $Cr^{VI}$ (μg) | Recovery (%) of $Cr^{VI}$ ± RSD | | | |
|---|---|---|---|---|
| | Two Fractions | Three Fractions | Four Fractions | Five Fractions |
| 10.0 | 85.3 ± 2.7 | 95.3 ± 3.3 | 95.5 ± 2.7 | 96.3 ± 2.4 |
| 20.0 | 83.1 ± 3.4 | 94.1 ± 3.7 | 94.9 ± 4.1 | 95.0 ± 2.9 |
| 40.0 | 83.9 ± 4.8 | 93.3 ± 3.6 | 94.5 ± 3.2 | 94.8 ± 2.8 |
| 80.0 | 82.5 ± 4.5 | 93.0 ± 4.2 | 94.1 ± 3.7 | 94.6 ± 3.4 |

"RSD" in the various Tables indicates the relative standard deviation of the samples (normally carried out in triplicate).

This data show that eluting with three fractions (3 ml for each fraction) of eluting solution allows for high recoveries (93.3 to 95.3%) and that no significant improvement in recoveries could be obtained by increasing the number of eluting fractions to more than three. Since a small volume of eluate is preferred to achieve a high enrichment factor, all the $Cr^{VI}$ concentrated on the cartridge should be eluted in as small a volume as possible. Each fraction of 3 ml ammonium sulfate buffer solution (pH 8) was tested and good results were obtained. Under these optimum conditions, recoveries from duplicate spike solutions exhibited reproducible results. It was also confirmed from these experiments that the presence of $Cr^{III}$ did not significantly affect $Cr^{VI}$ recovery. These really indicated that the conditions used stabilized both $Cr^{III}$ and $Cr^{VI}$ species.

These trials indicated that increasing either ammonium sulfate concentration above 0.5 M or using more than three eluting fractions did not significantly change $Cr^{VI}$ retention abilities. Therefore, an ammonium sulfate buffer of 0.5 M with 3 fractions (3 ml for each fraction) was found to give optimal elution power of $Cr^{VI}$ from these SAE cartridges.

As shown in Table I, relative standard deviations for the triplicate runs were between 2.4 and 4.8%. The limit of detection (LOD), estimated as the mass of analyte which gives a signal that is 3 times σ above the mean blank signal (where σ is the standard deviation of the blank signal), was about 1.0 ng/ml for the spectrometric determination. A calibration curve was obtained by using a linear plot of the peak area as a function of standard concentrations of $Cr^{VI}$ by least squares regression analysis.

Example 3

Ultrasonic Extraction of Soluble and Insoluble $Cr^{VI}$

Although the soluble fractions of $Cr^{VI}$ are useful parameters for estimating levels of $Cr^{VI}$ that may be directly absorbed by humans, quantifying insoluble forms of $Cr^{VI}$ is pertinent to occupational hazards (such as PbCrO4 in chromate ore processing and painting) associated with airborne respirable dust. Therefore, an effective and reliable method for extracting both soluble and insoluble forms of $Cr^{VI}$ without inducing $Cr^{III}$ oxidation or $Cr^{VI}$ reduction is required. Thus, it is important to evaluate ultrasonic extraction for the dissolution of both soluble $Cr^{VI}$ ($K_2CrO4$) and insoluble $Cr^{VI}$ ($PbCrO_4$) with basic buffer solutions. In this portion of the study, both ammonium sulfate and ammonium hydroxide buffer (pH 8) and/or Tris-HCl buffer solutions (with adjustment to pH 8 using $NH_4OH$) were used as the ultrasonic extraction buffer.

As noted above, a slightly basic ammonium buffer solution may help stabilization of chromium species in this system. Ammonium sulfate and ammonium hydroxide buffer solutions were used to dissolve hexavalent chromium from environmental matrices. It is expected that conditions of the hot ammonium buffer sonication procedure might oxidize $Cr^{III}$ to $Cr^{VI}$ under diverse redox conditions of various matrices. Hence no heating and relatively low concentration of the ammonium sulfate and ammonium hydroxide buffer solution (pH 8) were used to quantify and define operationally soluble and insoluble forms of $Cr^{VI}$.

To maximize dissolution of all forms of $Cr^{VI}$ while minimizing method-induced oxidation and reduction, an extraction protocol was employed using 0.05 M ammonium sulfate and ammonium hydroxide buffer solution with ultrasonication at temperatures lower than about 400° C. These conditions should maintain a low activity of $Cr^{III}$, thereby minimizing oxidation of this species to $Cr^{VI}$. Lead chromate ($PbCrO_4$, Ksp=$1.8 \times 10^{-14}$) was used to represent insoluble $Cr^{VI}$ because it contained a greater percentage of its total $Cr^{VI}$ in an insoluble form. In initial trials, 300 μg (w/w) of $PbCrO_4$, $K_2CrO_4$, and $Cr_2O_3$ were spiked into triplicate samples of the 10 ml 0.05 M ammonium sulfated and ammonium hydroxide buffer solution. Since this method does not employ a high temperature to dissolve insoluble forms of $Cr^{VI}$, it was hypothesized that it would minimize method-induced oxidation and reduction while effectively dissolving $Cr^{VI}$.

Despite the demonstrated efficacy of the ammonium sulfate solution to dissolve insoluble forms of $Cr^{VI}$ in solution while minimizing method-induced oxidation of $Cr^{III}$ or reduction of $Cr^{VI}$, a second procedure employing Tris-HCl buffer (with ammonium hydroxide adjustment to pH 8) ultrasonication dispersion was also tested in an attempt to quantify $Cr^{VI}$ in spiked solutions. As Tris-HCl, buffer contains ammonia, this ion can complex with $Cr^{III}$ and therefore may help stabilization of the trivalent chromium species.

Table II below shows the results for $Cr^{VI}$ recoveries from ammonium sulfate and Tris-HCL buffer solutions.

TABLE II

| Ultrasonic Buffer Solution | Recovery (%) of $Cr^{VI}$ ± RSD | |
|---|---|---|
| | Spiked $K_2CrO_4$ (300 μg/10 ml) | Spiked $PbCrO_4$ (300 μg/10 ml) |
| | Ultrasonication 30 min, Temp. <40° C. | |
| 0.02M $(NH_4)_2SO_4$ + 0.02M $NH_4OH$ | 94.5 ± 3.5 | 86.5 ± 3.1 |
| 0.05M $(NH_4)_2SO_4$ + 0.05M $NH_4OH$ | 94.3 ± 2.4 | 90.5 ± 2.9 |
| 0.02M Tris-HCl + $NH_4OH$ (pH 8) | 93.9 ± 3.8 | 82.5 ± 4.3 |
| 0.05M Tris-HCl + $NH_4OH$ (pH 8) | 93.7 ± 2.5 | 85.9 ± 3.6 |
| | Ultrasonication 60 min, Temp. <40° C. | |
| 0.02M $(NH_4)_2SO_4$ + 0.02M $NH_4OH$ | 94.4 ± 3.8 | 90.4 ± 3.9 |
| 0.05M $(NH_4)_2SO_4$ + 0.05M $NH_4OH$ | 95.5 ± 3.7 | 92.5 ± 4.7 |
| 0.05M Tris-HCl + $NH_4OH$ (pH 8) | 94.9 ± 4.9 | 89.5 ± 5.3 |

One hour sonication in ammonium sulfate and ammonium hydroxide buffer solution dissolved slightly greater quantities of lead chromate (92.5%) than Tris-HCl buffer (89.5%) under the same ultrasonic extraction conditions; however, these values are not statistically different (t-test, 95% C.I.). Based on the incomplete dissolution of lead chromate (Ksp=$1.8\times10^{-14}$), comparisons were made between lead chromate and potassium chromate both spiked into same buffer solutions. As indicated in Table II, $Cr^{VI}$ is more difficult to extract from chromate (recovery 90.5%) than with potassium chromate (95.1%) under the same ultrasonication time and temperature conditions. Similar results were observed for recoveries of soluble $Cr^{VI}$ spiked in Tris-HCl buffer. Close evaluation of the ultrasonication process revealed that lead chromate crystals were slowly dissolved, and this is evident in the nearly quantitative recoveries obtained from insoluble $Cr^{VI}$. In addition, it was noticed that extension of the ultrasonication period from 30 minutes to 60 min can enhance the dissolution of insoluble $Cr^{VI}$ and increase the recoveries from 90.5% to 92.6%.

Samples spiked with both soluble and insoluble $Cr^{III}$ and $Cr^{VI}$ were also evaluated. Ultrasonication was for 30 minutes at a temperature less than about 40° C. The results are shown in Table III below.

TABLE III

| Ultrasonic Buffer Solution | Recovery (%) of $Cr^{VI}$ ± RSD | | |
|---|---|---|---|
| | Spiked $K_2CrO_4$ (300 µg/ 10 ml) | Spiked $K_2CrO_4$ + $Cr^{III}$ (both at 300 µg/10 ml) | Spiked $PbCrO_4$ + $Cr_2O_3$ (both at 300 µg/10 ml) |
| 0.02M $(NH_4)_2SO_4$/ 0.02M $NH_4OH$ | 94.5 ± 3.5 | 94.0 ± 2.6 | 85.2 ± 3.7 |
| 0.05M $(NH_4)_2SO_4$/ 0.05M $NH_4OH$ | 95.3 ± 2.4 | 95.1 ± 3.9 | 89.2 ± 4.1 |
| 0.02M Tris-HCl + $NH_4OH$ (pH 8) | 93.9 ± 3.8 | 93.3 ± 2.8 | 83.0 ± 4.8 |
| 0.05M Tris-HCl + $NH_4OH$ (pH 8) | 94.7 ± 2.5 | 94.0 ± 3.6 | 95.1 ± 3.7 |

Neither method-induced reduction of $Cr^{VI}$ nor oxidation of $Cr^{III}$ was observed under these experimental conditions. When $Cr^{III}$ was present in solutions containing $Cr^{VI}$, $Cr^{VI}$ was essentially unchanged. Thus, the conditions used appear to stabilize both $Cr^{III}$ and $Cr^{VI}$ species.

Example 4

Analysis of Reference Materials

Three certified reference materials (CRMs) were chosen to evaluate the basic isolation and determination procedure of the present invention. One certified reference material, US EPA CRM 013-050 (paint chips) contained relatively high levels of total chromium (reference values 617.6 µg/g with a 95% confidence interval of 595 to 670 µg/g). Another bulk standard reference material, NIST SRM 1633a (coal fly ash) contained a much lower level of total chromium (196±6 µg/g). No standard or reference data appears to be available for the $Cr^{VI}$ content of these CRM samples. A third reference material, IRRM CRM 545, contained approximately 3 mg of total welding dust with about 100 µg of hexavalent chromium per filter sample. This last reference material has only just recently become available and appears to be the only known CRM for particulate hexavalent chromium.

In operation, 10 ml of 0.05 M ammonium sulfate and 0.05 M ammonium hydroxide (pH 8) buffer solution was added to about 1 g EPA CRM 013-50 paint chips or about 2 µg NIST SRM 1633a coal fly ash to release the hexavalent chromium by sonication. For the IRMM CRM 545 sample, the filters were sonicated in the same buffer solution. Following sonication, aliquots of extraction solution were subjected to solid phase extraction, complexation with diphenylcarbazide, and spectrophotometric detection. The analysis results showed that the hexavalent chromium content was 54.4±2.3 µg/g for EPA CRM 0134-50 paint chips, and 0.19±0.01 µg/g for NIST SRM 1633a coal fly ash. These values are virtually identical to those found in using a flow-injection analysis procedure (see Example 6 below and Wang et al., Analyst, 1997, 122, 1307–1313).

The recovery results for hexavalent chromium from IRMM CRM 545 are shown in Table IV.

TABLE IV

| | Certified Value for $Cr^{VI}$ in CRM 545 | | Experimental Value | | |
|---|---|---|---|---|---|
| | Welding | | | | |
| Sample | dust (µg/filter) | $Cr^{VI}$ (µg/mg) | $Cr^{VI}$ (µg/filter) | $Cr^{VI}$ (µg/filter) | Recovery (%) |
| 1 | 2.895 | 39.5 | 114.3 | 112.3 | 98.1 |
| 2 | 2.953 | 39.5 | 116.6 | 115.2 | 98.8 |
| 3 | 3.053 | 39.5 | 120.5 | 119.4 | 99.1 |
| 4 | 2.994 | 39.5 | 118.2 | 117.4 | 99.3 |
| 5 | 2.939 | 39.5 | 116.1 | 115.5 | 99.5 |
| Average | 2.967 | 39.5 | 117.1 ± 1.98 | 115.9 ± 2.33 | 99.0 ± 0.55 |

The recovery of hexavalent chromium from the IRMM CRM is quantitative (99%).

Example 5

Workplace Air Samples

This example illustrates the use of the present method to monitor $Cr^{VI}$ exposure at various aircraft painting and maintenance operations at U.S. Air Force bases. Air filters used to collect airborne particulate (including $Cr^{VI}$) were placed in a 15 ml plastic tube to which 10 ml of 0.05 M $(MH_4)_2SO_4$ and 0.05 M $NH_4OH$ (pH 8) buffer solution was added. This was followed by ultrasonication in an ultrasonic bath for 30 minutes (<40° C.). After ultrasonication, a portion (about 3 ml) of the supernatant obtained (total of about 10 ml) was loaded onto a strong anion exchange cartridge. Washing of the SAE cartridge was performed by flushing it with 3 ml deionized water. The $Cr^{VI}$ was eluted with 9 ml of 0.5 M $(NH_4)_2SO_4$ and 0.1 M $NH_4OH$ (pH 8) buffer solution in three fractions at about 2 ml/min. After isolation and purification by SAE-SPE, the eluate was acidified with 100 µl 37% HCl solution, followed by reaction with 2 ml of 20 mM 1,5-phenylcarbazine complexing reagent. The reaction of 1,5-diphenylcarbazide with $Cr^{VI}$ is completed in a few seconds.

Quantification of hexavalent chromium for the air filter samples was preformed using the standard addition method. A blank filter (non exposure) was used as a blank sample and was subjected to the same procedure as all other air samples, and analyzed with the same technique to check for any influence or baseline shift, and to ensure matrix matching. The linear dynamic range was 10 µg/l to 3.0 mg/l with a correlation coefficient ($R^2$) of 0.9991–0.9998 for all quality assurance/quality control samples (clean filters spiked with known quantities of hexavalent chromium). The calibration equation for the external standard or standard addition was calculated by linear regression.

The results obtained with these workplace air samples are shown in Table V below.

| Sample | $Cr^{VI}$ Content $\mu$g/sample | Air Volume | $\mu$g/m³ | Sample Location |
|---|---|---|---|---|
| 1 | 0.664 | 147.1 | 4.51 | Alodining F-16 |
| 2 | 0.707 | 72.67 | 9.73 | Alodining spray F016 (wipe and water rinse) |
| 3 | 1.034 | 126.1 | 8.19 | Cutting/grinding steel |
| 4 | 0.643 | 117.2 | 5.48 | Sanding C0130 beaver tail |
| 5 | 0.521 | 73.01 | 7.14 | Sanding F-16 bare metal |
| 6 | 2.952 | 191.5 | 15.41 | Sanding F-16 under wing & under couch |
| 7 | 4.175 | 192.1 | 21.73 | Sanding F-16 to bare metal under wing |
| 8 | 4.523 | 173.1 | 26.12 | Sanding F-16 landing gear |
| 9 | 2.678 | 72.45 | 36.97 | Sanding C-130 door edges |
| 10 | 2.224 | 59.03 | 37.67 | Sanding F-16 air intake |
| 11 | 3.641 | 36.04 | 101.02 | Priming F-16 yellow spray |
| 12 | 4.341 | 39.11 | 110.99 | Priming C-130 door |
| 13 | 6.922 | 67.01 | 103.32 | Priming F-16 |
| 14 | 6.567 | 39.53 | 166.12 | Priming F-16 |
| 15 | 8.535 | 48.91 | 174.51 | Priming C-130 |
| 16 | 34.41 | 136.5 | 252.08 | Priming F-16 |
| 17 | 20.84 | 79.01 | 263.76 | Priming C-130 cargo door |
| 18 | 6.822 | 25.28 | 269.86 | Priming water base |
| 19 | 14.18 | 39.02 | 363.65 | Priming F-16 landing gear |
| 20 | 8.011 | 19.86 | 403.37 | Priming small parts & panels |

The $Cr^{VI}$ contents detected reasonably match those expected in the various workplace locations. The highest contents of $Cr^{VI}$ were detected in paint priming operations (where the primers are known to contain high levels of $Cr^{VI}$), the lowest hexavalent chromium exposures were observed in alodining and cutting operations. Sanding gave rise to $Cr^{VI}$ exposures that were intermediate in hexavalent chromium content.

Example 6

Flow Injection Analysis

This example illustrates the use of flow injection analysis (FIA) using UV/VIS detection of the Cr-diphenylcarbazone complex. Except as noted, the general procedures and reagents used in the previous examples were employed here. (This procedure is described in more detail in Wang et al., Analyst, 1997, 122, 1307–1312, which is hereby incorporated by reference in its entirety). The flow injection system consisted of a Waters 600-MS system controller pump, a Waters 717 Plus autosampler (Millipore, Milford, Mass.), and a Model 783 programmable ultraviolet absorbance detector set at 540 nm (Applied Biosystems, Ramsey, N.J.). The flow rate of the pump was 1.0 ml/min for the mobile phase. Upon initial start up, the system was allowed to equilibrate for about 15 minutes. A sample volume of 10 $\mu$l was used for injections.

For elution, a 10 cm×1.5 cm id anion-exchange column containing 1.0 g resin was used. The strong anion-exchange resin was Dowex 1-X8 (Fluka Chemical, Ronkonkoma, N.Y.), a styrene-divinylbenzene polymer to which tertiary ammonium groups have been bound. The resin capacity was 1.3 mequiv/ml; the chloride form was used. The resin was cleaned prior to use by slurrying it with 3 M HCl, allowing it to stand for 10 minutes, and then decanting off the acid. This procedure was repeated three times. After pouring off the last portion of acid, the resin was slurried with 1 M HCl and dried prior to use.

This FIA-UV/VIS method was used on a variety of spiked samples, certified reference materials, and workplace samples. In general, the samples (spiked filters (0.8$\mu$, 37 mm), 1.0 g spiked sand, 0.1 g CRMs, and 1.0 g other fly ash and paint chip materials) were treated with 0.05 M $(NH_4)_2SO_4$-0.005 M $NH_3$ (pH 8.0) in an ultrasonic bath for 30 minutes at about 40° C. The samples were then subjected to anion exchange separation (1.0 g Dowex 1-X8). The eluate was acidified and reacted with 2 ml of 20 mM 1,5-diphenylcarbazide complexing solution. Finally, the $Cr^{VI}$ content was determined by flow injection analysis. The following results were obtained.

TABLE VI

| Sample | $Cr^{VI}$ ($\mu$g/g ± RSD) | Recovery (%) |
|---|---|---|
| Spiked filter - 40 $\mu$g/filter | 37.9 ± 3.2 | 95.6 |
| Spiked sand - 25 $\mu$g $Cr^{VI}$/g | 23.8 ± 4.5 | 95.2 |
| Spiked sand - 25 $\mu$g $Cr^{VI}$/g + 250 $\mu$g $Cr^{III}$/g | 23.3 ± 7.6 | 93.8 |
| EPA 013-050 CRM (paint chip) | 54.4 ± 3.4 | N/A |
| NIST 1633a CRM (coal fly ash) | 0.19 ± 3.9 | N/A |
| Power company coal fly ash | 0.53 ± 3.4 | N/A |
| Gas pipe paint chips | 352.6 ± 4.4 | N/A |
| Laboratory door paint chips | below detection limits | N/A |
| University building paint chips | below detection limits | N/A |

"N/A" in the Table indicates that no standard or reference data for $Cr^{VI}$ was available for those particular samples and that $Cr^{VI}$ recovery cannot be determined. The detection limit was estimated at 0.11 ng $Cr^{VI}$. The results for the two CRM samples are in good agreement with those reported in Example 4 above.

That which is claimed is:

1. A method for the detection of $Cr^{VI}$ in a sample, said method comprising:
   (1) ultrasonic extraction of $Cr^{VI}$ from the sample utilizing a first buffer solution having a pH of about 7.2 to 9.0, whereby the pH of the first buffer solution is such that neither significant $Cr^{III}$ oxidation nor $Cr^{VI}$ reduction occurs;
   (2) separation of the $Cr^{VI}$ in the ultrasonic extractant from step (1) from any $Cr^{III}$ or other interferents that might be present in the sample by passage of the ultrasonic extractant through a strong anion exchange solid phase extraction media;
   (3) elution of the $Cr^{VI}$ from the media with a second buffer solution having a pH of about 7.2 to 9.0;
   (4) acidification of the eluate containing the $Cr^{VI}$; and
   (5) addition of a complexing agent to the acidified eluate to form a colored $Cr^{VI}$ complex if $Cr^{VI}$ is present in the sample.

2. The method as defined in claim 1, wherein the first buffer solution contains $(NH_4)_2SO_4$ and $NH_4OH$ and the second buffer solution contains $(NH_4)_2SO_4$ and $NH_4OH$.

3. The method as defined in claim 2, wherein the first buffer solution contains about 0.02 M to 0.2 M $(NH_4)_2SO_4$ and about 0.02 M to 0.2 M $NH_3OH$ and the second buffer solution contains 0.25 M to 1.0 M $(NH_4)_2SO_4$ and about 0.25 M to 1.0 M $NH_4OH$.

4. The method as defined in claim 2, wherein the first buffer solution contains about 0.025 M to 0.1 M $(NH_4)_2SO_4$ and about 0.025 M to 0.1 M $NH_4OH$ and the second buffer solution contains 0.25 M to 1.0 M $(NH_4)_2SO_4$ and about 0.25 M to 1.0 M $NH_4OH$.

5. The method as defined in claim 2, wherein the first buffer solution contains about 0.05 M $(NH_4)_2SO_4$ and about 0.05 M $NH_4OH$ and the second buffer solution contains about 0.5 M $(NH_4)_2SO_4$ and about 0.5 M $NH_4OH$.

6. The method as defined in claim 1, wherein the strong anion exchange solid phase extraction media is a quaternary amine bonded silica with Cl⁻ as the counter ion.

7. The method as defined in claim 4, wherein the strong anion exchange solid phase extraction media is a quaternary amine bonded silica with Cl⁻ as the counter ion.

8. The method as defined in claim 1, wherein the complexing agent is 1,5-diphenylcarbazide.

9. The method as defined in claim 7, wherein the complexing agent is 1,5-diphenylcarbazide.

10. The method as defined in claim 1, further comprising subjecting the colored $Cr^{VI}$-complex, if present, from step (5) to a spectrophotometric analysis to determine the amount of $Cr^{VI}$ present in the sample.

11. The method as defined in claim 9, further comprising subjecting the colored $Cr^{VI}$-complex, if present, from step (5) to a spectrophotometric analysis to determine the amount of $Cr^{VI}$ present in the sample.

12. A method for the quantitative detection of $Cr^{VI}$ in a sample suspected of containing $Cr^{VI}$, said method comprising:

(1) ultrasonic extraction of $Cr^{VI}$ from the sample utilizing a first ammonium buffer solution having a pH of about 7.2 to 9.0, whereby the pH of the ammonium buffer solution is such that neither significant $Cr^{III}$ oxidation nor $Cr^{VI}$ reduction occurs;

(2) separation of the $Cr^{VI}$ in the ultrasonic extract from step (1) from any $Cr^{III}$ or other interferents that might be present in the sample by passage of the ultrasonic extractant through a strong anion exchange solid phase extraction media;

(3) elution of the $Cr^{VI}$ from the media with a second ammonium buffer solution;

(4) acidification of the eluate containing $Cr^{VI}$;

(5) addition of 1,5-diphenylcarbazide to the acidified eluate to form a colored $Cr^{VI}$-1,5-diphenylcarbazone complex if $Cr^{VI}$ is present in the sample; and (6) subjecting the $Cr^{VI}$-1,5-diphenylcarbazone complex, if present, from step (5) to a spectrophotometric analysis in order to determine the amount of $Cr^{VI}$ present in the sample.

13. The method as defined in claim 2, wherein the first buffer solution contains $(NH_4)_2SO_4$ and $NH_4OH$ and the second buffer solution contains $(NH_4)_2SO_4$ and $NH_4OH$.

14. The method as defined in claim 13, wherein the first buffer solution contains about 0.02 M to 0.2 M $(NH_4)_2SO_4$ and about 0.02 M to 0.2 M $NH_4OH$ and the second buffer solution contains 0.25 M to 1.0 M $(NH_4)_2SO_4$ and about 0.25 M to 1.0 M $NH_4OH$.

15. The method as defined in claim 13, wherein the first buffer solution contains about 0.025 M to 0.1 M $(NH_4)_2SO_4$ and about 0.025 M to 0.1 M $NH_4OH$ and the second buffer solution contains 0.25 M to 1.0 M $(NH_4)_2SO_4$ and about 0.25 M to 1.0 M $NH_4OH$.

16. The method as defined in claim 13, wherein the first buffer solution contains about 0.05 M $(NH_4)_2SO_4$ and about 0.05 M $NH_4OH$ and the second buffer solution contains about 0.5 M $(NH_4)_2SO_4$ and about 0.5 M $NH_4OH$.

17. The method as defined in claim 12, wherein the strong anion exchange solid phase extraction media is a quaternary amine bonded silica with Cl⁻ as the counter ion.

18. The method as defined in claim 15, wherein the strong anion exchange solid phase extraction media is a quaternary amine bonded silica with Cl⁻ as the counter ion.

19. The method as defined in claim 16, wherein the strong anion exchange solid phase extraction media is a quaternary amine bonded silica with Cl⁻ as the counter ion and is contained in a pre-made cartridge.

* * * * *